United States Patent [19]

Suzuki et al.

[11] Patent Number: 4,460,773
[45] Date of Patent: Jul. 17, 1984

[54] 1-PHENYL-1H-PYRAZOLO [3,4-B]PYRAZINE DERIVATIVES AND PROCESS FOR PREPARING SAME

[75] Inventors: Shinichi Suzuki, Odawara; Kunitomo Suzuki, Hatano; Hiromitsu Honda, Yamanishi, all of Japan

[73] Assignee: Lion Corporation, Tokyo, Japan

[21] Appl. No.: 428,016

[22] Filed: Sep. 29, 1982

[30] Foreign Application Priority Data

Feb. 5, 1982 [JP] Japan .................................. 57-17227
Apr. 16, 1982 [JP] Japan .................................. 57-63675
Apr. 16, 1982 [JP] Japan .................................. 57-63676

[51] Int. Cl.³ .................. C07D 487/04; A61K 31/495
[52] U.S. Cl. .................................. 544/350; 424/250; 544/118; 544/357
[58] Field of Search ........................................ 544/350

[56] References Cited

U.S. PATENT DOCUMENTS 3,957,782   5/1978   Hoehn Hans ...................... 544/350
4,303,658  12/1981   Paris et al. ........................ 544/350

OTHER PUBLICATIONS

Guarreri et al., Chem. Abstract 71, 81306v.

Primary Examiner—Mark L. Berch
Attorney, Agent, or Firm—Armstrong, Nikaido, Marmelstein & Kubovcik

[57] ABSTRACT

Novel 1-phenyl-1H-pyrazolo[3,4-b]pyrazine derivatives are provided which are represented by the formula:

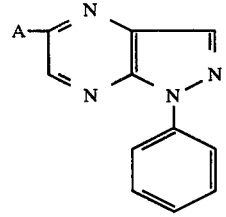

wherein A is (i)

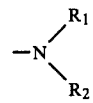

in which $R_1$ and $R_2$ are hydrogen or an alkyl, substituted alkyl, cycloalkyl, substituted cycloalkyl or amino group, or a divalent radical forming a nitrogen-containing saturated heterocyclic ring together with the nitrogen atom, (ii)

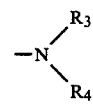

wherein $R_3$ is a phenyl group which is unsubstituted or substituted by halogen or a lower alkyl, lower alokoxy, carboxyl or nitro group, and $R_4$ is halogen or a methyl or ethyl group, (iii)—$OR_5$ in which $R_5$ is a phenyl group which is unsubstituted or substituted by halogen or a hydroxyl, lower alkyl, lower alkoxy, amino or lower alkylamide group, or (iv)—$OR_6$ is an alkyl group which is unsubstituted or substituted by halogen or a phenyl, furanyl, tetrahydrofuranyl or alkylamino group. These derivatives have antitumor or antiviral activity.

5 Claims, No Drawings

1-PHENYL-1H-PYRAZOLO [3,4-B]PYRAZINE DERIVATIVES AND PROCESS FOR PREPARING SAME

BACKGROUND OF THE INVENTION

1. Field of the Invention

The present invention relates to a 1-phenyl-1H-pyrazolo[3,4-b]pyrazine derivative having excellent antitumor or antiviral activity, which is represented by the following formula (1):

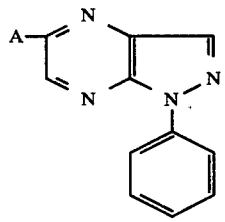
(1)

In the above formula (1), A stands for (i) a group

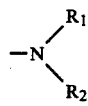

in which $R_1$ and $R_2$ stand for a hydrogen atom, a univalent group selected from an alkyl group, a substituted alkyl group, a cycloalkyl group, a substituted cycloalkyl group and an amino group or a divalent group forming a substituted or unsubstituted, nitrogen-containing saturated heterocyclic ring together with the nitrogen atom: (ii) a group

in which $R_3$ stands for a phenyl group or a substituted phenyl group in which at least one hydrogen atom is substituted by a halogen atom, a lower alkyl group, a lower alkoxy group, a carboxyl group or a nitro group, and $R_4$ stands for a hydrogen atom, or a methyl or ethyl group; (iii) a group —$OR_5$ in which $R_5$ stands for a phenyl group or a substituted phenyl group in which at least one hydrogen atom is substituted by a halogen atom, a hydroxyl group, a lower alkyl group, a lower alkoxy group, an amino group or a lower alkylamide group; or (iv) a group —$OR_6$ in which $R_6$ stands for an alkyl group, a cycloalkyl group or a substituted alkyl group in which at least one hydrogen atom is substituted by a halogen atom, a substituted or unsubstituted phenyl group, a furanyl group, a tetrahydrofuranyl group or an alkylamino group.

2. Description of the Prior Art

Various substances having antitumor and antiviral activities have been developed and proposed. We made researches with a view to developing a compound having an antitumor or antiviral activity and capable of being used as an antitumor or antiviral agent, and as the result, we succeeded in synthesizing noval 1-phenyl-1H-pyrazolo[3,4-b]pyrazine derivatives represented by the above formula (1) and found that these compounds have excellent antitumor and antiviral activities and are useful as an antitumor or antiviral agent.

SUMMARY OF THE INVENTION

The novel compounds of the present invention, that is, 1-phenyl-1H-pyrazol[3,4-b]pyrazine derivatives have a chemical structure represented by the following formula (1):

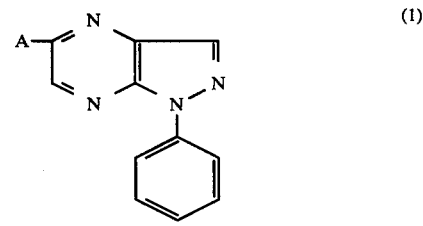
(1)

wherein A stands for a group

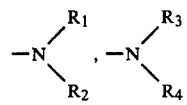

—$OR_5$ or —$OR_6$ and $R_1$ through $R_6$ are as defined above.

DETAILED DESCRIPTION OF THE PREFERRED EMBODIMENTS

When A in the formula (1) stands for a group

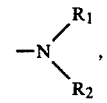

as the alkyl group constituting the groups $R_1$ and $R_2$, there can be mentioned, for example, linear alkyl groups having 1 to 10 carbon atoms, such as methyl, ethyl, propyl, butyl, pentyl, hexyl and decanyl groups, and branched alkyl groups having 1 to 10 carbon atoms, such as 1-methylethyl, 2-methylpropyl, 1-methylpropyl, 1,1-dimethylethyl, 2-methylbutyl, 3-methylbutyl, 1,1-dimethylpropyl, 2,2-dimethylpropyl, 1-methylbutyl, 1-methylpentyl, 2-methylpentyl, 3-methylpentyl, 4-methylpentyl, 1,3-dimethylbutyl, 1,2-dimethylbutyl, 2,3-dimethylbutyl, 2,2-dimethylbutyl, 3,3-dimethylbutyl, 1-ethylbutyl, 2-ethylbutyl, 1-methylhexyl and 1-methylheptyl groups.

As the substituted alkyl group, there can be mentioned, for example, alkyl groups as exemplified above, in which at least one hydrogen atom is substituted by a hydroxyl group, a carboxyl group, a halogen atom, a lower alkylamino group, a phenyl group or a substituted phenyl group. As the halogen atom, there can be mentioned fluorine, chlorine and bromine, and as the alkyl group of the lower alkylamino group, there can be mentioned, for example, linear and branched alkyl groups having 1 to 6 carbon atoms, such as methyl, ethyl, propyl, isopropyl, butyl, isobutyl, pentyl, isopentyl, neopentyl and hexyl groups. The substituted phenyl group is a phenyl group in which at least one hydrogen atom is substituted by an appropriate substituent. As the substituent, there can be mentioned, for example, linear and branched lower alkyl groups having 1 to 6 carbon atoms, such as methyl, ethyl, propyl, isopropyl, butyl, isobutyl, pentyl, isopentyl, neopentyl and hexyl groups, halogen atoms such as fluorine, chlorine and bromine, a nitro group and a carboxyl group.

As the cycloalkyl group, there can be mentioned cycloalkyl groups having 5 to 8 carbon atoms, for example, cyclopentyl and cyclohexyl groups.

As the nitrogen-containing sauturated heterocyclic ring, there can be mentioned, for example, pyrrolidinyl, imidazolidinyl, pyrazolidinyl, piperidinyl, piperazinyl and morpholinyl groups.

These cycloalkyl and nitrogen-containing saturated heterocyclic groups may have at least one hydrogen atom thereof substituted by an appropriate substituent. As the substituent, there can be mentioned, for example, a hydroxyl group, linear and branched lower alkyl groups having 1 to 6 carbon atoms, such as methyl, ethyl, propyl, isopropyl, butyl, isobutyl, pentyl, isopentyl, neopentyl and hexyl groups, halogen atoms such as fluorine, chlorine and bromine, and a nitro group and a carboxyl group.

The groups $R_1$ and $R_2$ in A are preferably a hydrogen atom or a linear or branched alkyl group having 3 to 7 carbon atoms.

When A in the formula (1) stands for a group

as the lower alkyl group constituting a substituent of the substituted phenyl group in $R_3$, there can be mentioned, for example, linear and branched alkyl groups having 1 to 6 carbon atoms, such as methyl, ethyl, propyl, isopropyl, butyl, isobutyl, pentyl, isopentyl and neopentyl groups. As the lower alkoxy group constituting a substituent of the substituted phenyl group in $R_3$, there can be mentioned, for example, linear and branched alkoxy groups having 1 to 6 carbon atoms, such as methoxy, ethoxy, propoxy, butoxy, pentyloxy and hexyloxy groups.

The group $R_3$ in A is preferably a phenyl group which is unsubstituted or substituted by a halogen atom or an alkyl group having 1 to 4 carbon atoms.

When A in the formula (1) stands for a group $-OR_5$, as the lower alkyl and lower alkoxy groups constituting substituents of the substituted phenyl group, there can be mentioned, for example, lower alkyl and lower alkoxy groups exemplified above with respect to $R_3$. As the lower alkylamide group, there can be mentioned, for example, linear and branched alkylamide groups having 1 to 6 carbon atoms, such as acetamide, propionamide and butylamide groups. The group $R_5$ is preferably a phenyl group which is unsubstituted or substituted by a halogen atom or an alkyl group having 1 to 4 carbon atoms.

When A in the formula (1) stands for a group $-OR_6$, as the alkyl, cycloalkyl and substituted alkyl groups, there can be mentioned, for example, alkyl, cycloalkyl and substituted alkyl groups exemplified above with respect to $R_1$ and $R_2$. The group $R_6$ is preferably an alkyl group having 1 to 7 carbon atoms.

The compound of the formula (1) in which A stands for a group

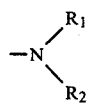

can be prepared by reacting 5-substituted-1-phenyl-1H-pyrazolo[3,4-b]pyrazine of the formula (2) with the corresponding amine or nitrogen-containing heterocyclic ring compound as expressed by the following reaction formula (a):

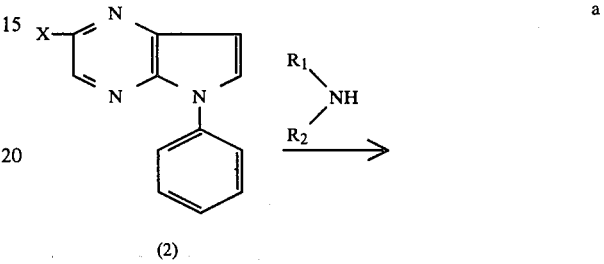

wherein X stands for a halogen atom, a group $-SO_2R$ (R is a lower slkyl group having 1 to 6 carbon atoms, a phenyl group, a methylphenyl group or an ethylphenyl group), a group $-NO_2$ or a group $-CN$, and $R_1$ and $R_2$ are as defined above.

The above-mentioned reaction (a) is carried out preferably at a temperature of 200° to 250° C. for 1 to 3 hours in a sealed tube which has been flushed with nitrogen, while an excessive amount of the amine or nitrogen-containing heterocyclic ring compound is used.

A compound of the formula (2) in which X is a chlorine atom, that is, 5-chloro-1-phenyl-1H-pyrazolo[3,4-b]pyrazine represented by the formula (2') given below, may be obtained, for example, according to the following reaction formula (b) by decarboxylation of 5-amino-1-phenylpyrazole-4-carboxylic acid of the formula (3) by heating at, for example, 180° C. to prepare 5-amino-1-phenylpyrazole of the formula (4), reaction of this compound with isoamyl nitrite in ethanol in the presence of dry hydrochloric acid to form 5-amino-4-nitroso-1-phenylpyrazole hydrochloride of the formula (5), catalytic reduction of this hydrochloride with palladium-carbon to prepare 4,5-diamino-1-phenylpyrazole of the formula (6), reaction of this compound with glyoxylic acid in water to prepare 4,5-dihydro-1-phenyl-1H-pyrazole[3,4-b]pyrazin-5-one of the formula (7) and refluxing of this compound with phosphorus oxychloride:

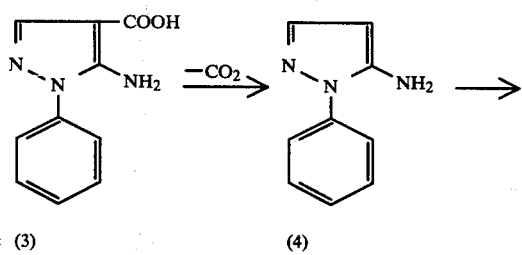

(3)      (4)

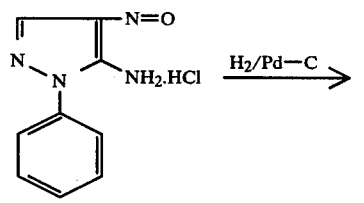

(5)

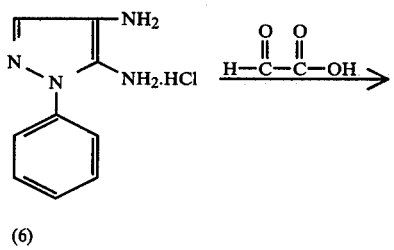

(6)

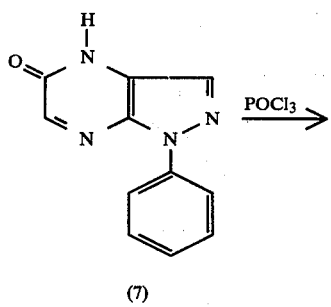

(7)

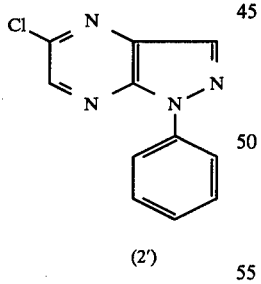

(2')

A compound of the formula (1) in which A stands for a group

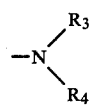

may be prepared by reacting 5-substituted-1-phenyl-1H-pyrazolo[3,4-b]pyrazine with a substituted or unsubstituted phenylamine according to the following reaction formula (a'):

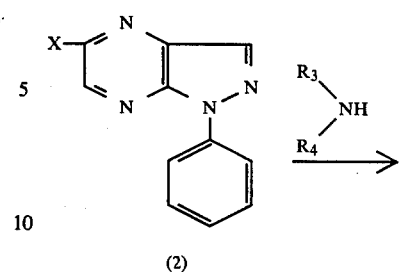

(2)

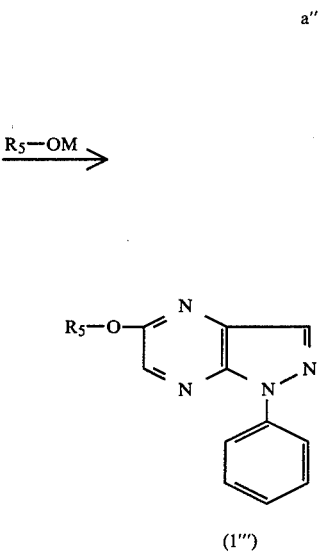

(1'')

wherein X stands for a halogen atom, a group —SO₂R (R stands for a lower alkyl group having 1 to 6 carbon atoms, a phenyl group, a methylphenyl group, or an ethylphenyl group), a group —NO₂ or a group —CN, and R₃ and R₄ are as defined above.

The above-mentioned reaction (a') is carried out preferably at a temperature of 200° to 250° C. for 1 to 3 hours in a sealed tube which has been flushed with nitrogen, while an excessive amount of the phenylamine is used.

A compound of the formula (1) in which A is a group —OR₅ may be prepared by reacting a 5-substituted-1-phenyl-1H-pyrozolo[3,4b]pyrazine of the formula (2) with the corresponding phenol derivative according to the following reaction formula (a''):

(2)

(1''')

wherein X stands for a halogen atom, a group —SO₂—R' (R' stands for an alkyl group having 1 to 6 carbon atoms, a phenyl group, a methylphenyl group or an ethylphenyl group), a group —NO₂ or a group —CN, M is an alkali metal such as Na or K, and R₅ is as defined above.

The above-mentioned reaction (a″) is carried out preferably at a temperature of 100° to 150° C. for 1 to 3 hours in dimethylsulfoxide or an alcohol while an excessive amount of the alcoholate $R_5$—OM is used.

A compound of the formula (1) in which A is a group —$OR_6$ may be prepared by reacting a 5-substituted-1-phenyl-1H-pyrazolo[3,4-b]pyrazine of the formula (2) with the corresponding alcoholate according to the following reaction formula (a″″):

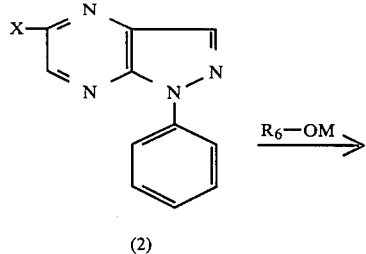

(2)

$R_6$—OM →

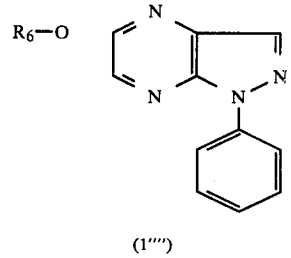

(1″″)

wherein X stands for a halogen atom, a group —$SO_2$—R′ (R′ stands for an alkyl group having 1 to 6 carbon atoms, a phenyl group, a methylphenyl group or an ethylphenyl group), a group —$NO_2$ or a group —CN, M is an alkali metal such as Na or K and $R_6$ is the same as defined above.

The above-mentioned reaction (a″″) may preferably be carried out under conditions similar to those which are described hereinbefore with respect to the reaction (a″).

Specific examples of the compound of the present invention represented by the above-mentioned formula (1) will now be described.

$$(1) \ A = -N\begin{matrix}R_1\\R_2\end{matrix}$$

| Compound No. | $R_1$ | $R_2$ | Name of Compound | Example No. |
|---|---|---|---|---|
| 1 | $C_3H_7$— | H— | 5-propylamino-1-phenyl-1H—pyrazolo[3,4-b]pyrazine | 1 |
| 2 | $C_4H_9$— | H— | 5-butylamino-1-phenyl-1H—pyrazolo[3,4-b]pyrazine | 2 |
| 3 | $C_5H_{11}$— | H— | 5-pentylamino-1-phenyl-1H—pyrazolo[3,4-b]pyrazine | 3 |
| 4 | $C_6H_{13}$— | H— | 5-hexylamino-1-phenyl-1H—pyrazolo[3,4-b]pyrazine | 4 |
| 5 | $C_{10}H_{21}$— | H— | 5-decanylamino-1-phenyl-1H—pyrazolo[3,4-b]pyrazine | 5 |
| 6 | HO—$C_2H_4$— | H— | 5-(2-hydroxyethylamino)-1-phenyl-1H—pyrazolo[3,4-b]-pyrazine | 6 |
| 7 | $CH_3\overset{OH}{\underset{|}{C}}HCH_2$— | H— | 5-(2-hydroxypropylamino)-1-phenyl-1H—pyrazolo[3,4-b]-pyrazine | 7 |
| 8 | $\begin{matrix}CH_3CH_2\\ \phantom{CH_3}CH-\\CH_3\end{matrix}$ | H— | 5-(1-methylpropylamino)-1-phenyl-1H—pyrazolo[3,4-b]-pyrazine | 8 |
| 9 | $C_4H_9\overset{C_2H_5}{\underset{|}{C}}HCH_2$— | H— | 5-(2-ethylhexylamino)-1-phenyl-1H—pyrazolo[3,4-b]-pyrazine | 9 |
| 10 | HOOC—$(CH_2)_3$— | H— | 5-(3-carboxypropylamino)-1-phenyl-1H—pyrazolo[3,4-b]-pyrazine | 10 |
| 11 | HOOC—$(CH_2)_5$— | H— | 5-(5-carboxypentylamino)-1-phenyl-1H—pyrazolo[3,4-b]-pyrazine | 11 |
| 12 | Cl—$(CH_2)_2$— | H— | 5-(2-chloroethylamino)-1-phenyl-1H—pyrazolo[3,4-b]-pyrazine | 12 |

-continued $$(1)\ A = -N\diagdown\genfrac{}{}{0pt}{}{R_1}{R_2}$$

| Compound No. | R₁ | R₂ | Name of Compound | Example No. |
|---|---|---|---|---|
| 13 | (CH₃)₂N—(CH₂)₂— | H— | 5-(2-N,N—dimethylamino-ethylamino)-1-phenyl-1H—pyrazolo[3,4-b]pyrazine | 13 |
| 14 | C₆H₅—CH₂— | H— | 5-benzylamino-1-phenyl-1H—pyrazolo[3,4-b]pyrazine | 14 |
| 15 | NO₂—C₆H₄—CH₂— | H— | 5-(4-nitrobenzylamino)-1-phenyl-1H—pyrazolo[3,4-b]-pyrazine | 15 |
| 16 | Cl—C₆H₄—CH₂— | H— | 5-(4-chlorobenzylamino)-1-phenyl-1H—pyrazolo[3,4-b]-pyrazine | 16 |
| 17 | 3-CH₃—C₆H₄—CH₂— | H— | 5-(3-methylbenzylamino)-1-phenyl-1H—pyrazolo[3,4-b]-pyrazine | 17 |
| 18 | C₄H₉— | C₄H₉— | 5-dibutylamino-1-phenyl-1H—pyrazolo[3,4-b]pyrazine | 18 |
| 19 | HO—(CH₂)₂— | CH₃— | 5-(2-hydroxymethylamino)-1-phenyl-1H—pyrazolo[3,4-b]-pyrazine | 19 |
| 20 | C₆H₅—CH₂— | CH₃— | 5-benzylmethylamino-1-phenyl-1H—pyrazolo[3,4-b]pyrazine | 20 |
| 21 | cyclopentyl— | H— | 5-cyclopentylamino-1-phenyl-1H—pyrazolo 8 3,4-b]pyrazine | 21 |
| 22 | cyclohexyl— | H— | 5-cyclohexylamino-1-phenyl-1H—pyrazolo[3,4-b]pyrazine | 22 |
| 23 | 4-CH₃—cyclohexyl— | H— | 5-(4-methylcyclohexylamino)-1-phenyl-1H—pyrazolo[3,4-b]-pyrazine | 23 |
| 24 | NH₂— | H— | 5-hydrazino-1-phenyl-1H—pyrazolo[3,4-b]pyrazine | 24 |
| 25 | piperidino— | | 5-piperidino-1-phenyl-1H—pyrazolo[3,4-b]pyrazine | 25 |

-continued (1) A = —N(R₁)(R₂)

| Compound No. | R₁ | R₂ | Name of Compound | Example No. |
|---|---|---|---|---|
| 26 | 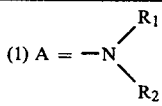 HOOC— | | 5-(3-carboxypiperidion)-1-phenyl-1H—pyrazolo[3,4-b]pyrazine | 26 |
| 27 | 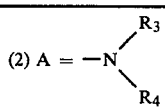 | | 5-morpholino-1-phenyl-1H—pyrazolo[3,4-b]pyrazine | 27 |

(2) A = —N(R₃)(R₄)

| Compound No. | R₃ | R₄ | Name of Compound | Example No. |
|---|---|---|---|---|
| 28 | phenyl | —H | 5-anilino-1-phenyl-1H—pyrazolo[3,4-b]pyrazine | 28 |
| 29 | phenyl | —CH₃ | 5-N—methylanilino-1-phenyl-1H—pyrazolo[3,4-b]pyrazine | 29 |
| 30 | 2-CH₃-phenyl | —H | 5-(2-toluidino)-1-phenyl-1H—pyrazolo[3,4-b]pyrazine | 30 |
| 31 | 3-CH₃-phenyl | —H | 5-(3-toluidino)-1-phenyl-1H—pyrazolo[3,4-b]pyrazine | 31 |
| 32 | 4-CH₃-phenyl | —H | 5-(4-toluidino)-1-phenyl-1H—pyrazolo[3,4-b]pyrazine | — |
| 33 | 2-OCH₃-phenyl | —H | 5-(2-anisidino)-1-phenyl-1H—pyrazolo[3,4-b]pyrazine | 34 |
| 34 | 3-OCH₃-phenyl | —H | 5-(3-anisidino)-1-phenyl 1H—pyrazolo[3,4-b]pyrazine | — |
| 35 | 4-OCH₃-phenyl | —H | 5-(4-anisidino)-1-phenyl-1H—pyrazolo[3,4-b]pyrazine | — |

-continued (2) A = 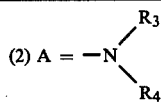

| Compound No. | R₃ | R₄ | Name of Compound | Example No. |
|---|---|---|---|---|
| 36 | 2-OC₂H₅-phenyl | —H | 5-(2-phenetidino)-1-phenyl-1H—pyrazolo[3,4-b]pyrazine | — |
| 37 | 3-OC₂H₅-phenyl | —H | 5-(3-phenetidino)-1-phenyl-1H—pyrazolo[3,4-b]pyrazine | — |
| 38 | 4-OC₂H₅-phenyl | —H | 5-(4-phenetidino)-1-phenyl-1H—pyrazolo[3,4-b]pyrazine | 35 |
| 39 | 2-Cl-phenyl | —H | 5-(2-chloroanilino)-1-phenyl-1H—pyrazolo[3,4-b]pyrazine | — |
| 40 | 3-Cl-phenyl | —H | 5-(3-chloroanilino)-1-phenyl-1H—pyrazolo[3,4-b]pyrazine | — |
| 41 | 4-Cl-phenyl | —H | 5-(4-chloroanilino)-1-phenyl-1H—pyrazolo[3,4-b]pyrazine | 36 |
| 42 | 2-F-phenyl | —H | 5-(2-fluoroanilino)-1-phenyl-1H—pyrazolo[3,4-b]pyrazine | — |
| 43 | 3-F-phenyl | —H | 5-(3-fluoroanilino)-1-phenyl-1H—pyrazolo[3,4-b]pyrazine | — |
| 44 | 4-F-phenyl | —H | 5-(4-fluoroanilino)-1-phenyl-1H—pyrazolo[3,4-b]pyrazine | 37 |
| 45 | 2-Br-phenyl | —H | 5-(2-bromoanilino)-1-phenyl-1H—pyrazolo[3,4-b]pyrazine | — |
| 46 | 3-Br-phenyl | —H | 5-(3-bromoanilino)-1-phenyl-1H—pyrazolo[3,4-b]pyrazine | — |
| 47 | 4-Br-phenyl | —H | 5-(4-bromoanilino)-1-phenyl-1H—pyrazolo[3,4-b]pyrazine | — |

-continued (2) A = —N⟨$R_3$/$R_4$

| Compound No. | $R_3$ | $R_4$ | Name of Compound | Example No. |
|---|---|---|---|---|
| 48 | 2-NO$_2$-C$_6$H$_4$- | —H | 5-(2-nitroanilino)-1-phenyl-1H—pyrazolo[3,4-b]pyrazine | — |
| 49 | 3-O$_2$N-C$_6$H$_4$- | —H | 5-(3-nitroanilino)-1-phenyl-1H—pyrazolo[3,4-b]pyrazine | 38 |
| 50 | 4-O$_2$N-C$_6$H$_4$- | —H | 5-(4-nitroanilino)-1-phenyl-1H—pyrazolo[3,4-b]pyrazine | — |
| 51 | 2-C$_2$H$_2$-C$_6$H$_4$- | —H | 5-(2-ethylanilino)-1-phenyl-1H—pytrazolo[3,4-b]pyrazine | — |
| 52 | 3-H$_5$C$_2$-C$_6$H$_4$- | —H | 5-(3-ethylanilino)-1-phenyl-1H—pyrazolo[3,4-b]pyrazine | — |
| 53 | 4-H$_5$C$_2$-C$_6$H$_4$- | —H | 5-(4-ethylanilino)-1-phenyl-1H—pyrazolo[3,4-b]pyrazine | — |
| 54 | 2-C$_3$H$_7$-C$_6$H$_4$- | —H | 5-(2-propylanilino)-1-phenyl-1H—pyrazolo[3,4-b]pyrazine | — |
| 55 | 3-H$_7$C$_3$-C$_6$H$_4$- | —H | 5-(3-propylanilino)-1-phenyl-1H—pyrazolo[3,4-b]pyrazine | — |
| 56 | 4-H$_7$C$_3$-C$_6$H$_4$- | —H | 5-(4-propylanilino)-1-phenyl-1H—pyrazolo[3,4-b]pyrazine | — |
| 57 | 2-C$_4$H$_9$-C$_6$H$_4$- | —H | 5-(2-butylanilino)-1-phenyl-1H—pyrazolo[3,4-b]pyrazine | |
| 58 | 3-H$_9$C$_4$-C$_6$H$_4$- | —H | 5-(3-butylanilino)-1-phenyl-1H—pyrazolo[3,4-b]pyrazine | 33 |
| 59 | 4-H$_9$C$_4$-C$_6$H$_4$- | —H | 5-(4-butylanilino)-1-phenyl-1H—pyrazolo[3,4-b]pyrazine | — |

-continued (2) A = $-N\diagup^{R_3}_{\diagdown R_4}$

| Compound No. | $R_3$ | $R_4$ | Name of Compound | Example No. |
|---|---|---|---|---|
| 60 | 2-COOH-phenyl | —H | 5-(2-carboxyanilino)-1-phenyl-1H—pyrazolo[3,4-b]pyrazine | — |
| 61 | 3-HOOC-phenyl | —H | 5-(3-carboxyanilino)-1-phenyl-1H—pyrazolo[3,4-b]pyrazine | — |
| 62 | 4-HOOC-phenyl | —H | 5-(4-carboxyanilino)-1-phenyl-1H—pyrazolo[3,4-b]pyrazine | — |
| 63 | 2,3-(CH$_3$)$_2$-phenyl | —H | 5-(2,3-dimethylanilino)-1-phenyl-1H—pyrazolo[3,4-b]pyrazine | 33 |
| 64 | 2,4-(CH$_3$)$_2$-phenyl | —H | 5-(2,4-dimethylanilino)-1-phenyl-1H—pyrazolo[3,4-b]pyrazine | — |
| 65 | 2,5-(CH$_3$)$_2$-phenyl | —H | 5-(2,5-dimethylanilino)-1-phenyl-1H—pyrazolo[3,4-b]pyrazine | — |
| 66 | 2,6-(CH$_3$)$_2$-phenyl | —H | 5-(2,6-dimethylanilino)-1-phenyl-1H—pyrazolo[3,4-b]pyrazine | — |
| 67 | 3,4-(CH$_3$)$_2$-phenyl | —H | 5-(3,4-dimethylanilino)-1-phenyl-1H—pyrazolo[3,4-b]pyrazine | — |
| 68 | 3,5-(CH$_3$)$_2$-phenyl | —H | 5-(3,5-dimethylanilino)-1-phenyl-1H—pyrazolo[3,4-b]pyrazine | — |

(3) A = —OR$_5$

| Compound No. | $R_5$ | Name of Compound | Example No. |
|---|---|---|---|
| 69 | phenyl | 5-phenoxy-1-phenyl-1H—pyrazolo[3,4-b]pyrazine | 39 |
| 70 | 4-CH$_3$-phenyl | 5-(4-methylphenoxy)-1-phenyl-1H—pyrazolo[3,4-b]pyrazine | 40 |

-continued

(3) A = —OR$_5$

| Compound No. | R$_5$ | Name of Compound | Example No. |
|---|---|---|---|
| 71 | (CH$_3$)$_2$HC—C$_6$H$_4$— | 5-(4-isopropylphenoxy)-1-phenyl-1H—pyrazolo[3,4-b]pyrazine | 41 |
| 72 | H$_2$N—C$_6$H$_4$— (3-) | 5-(3-aminophenoxy)-1-phenyl-1H—pyrazolo[3,4-b]pyrazine | 42 |
| 73 | H$_3$C—C(=O)—NH—C$_6$H$_4$— | 5-(4-acetoamidophenoxy)-1-phenyl-1H—pyrazolo[3,4-b]pyrazine | 43 |
| 74 | 2-CH$_3$O—C$_6$H$_4$— | 5-(2-methoxyphenoxy)-1-phenyl-1H—pyrazolo[3,4-b]pyrazine | 44 |
| 75 | H$_3$CO—C$_6$H$_4$— | 5-(4-methoxyphenoxy)-1-phenyl-1H—pyrazolo[3,4-b]pyrazine | 45 |
| 76 | H$_5$C$_2$O—C$_6$H$_4$— | 5-(4-ethoxyphenoxy)-1-phenyl-1H—pyrazolo[3,4-b]pyrazine | 46 |
| 77 | HO—C$_6$H$_4$— | 5-(4-hydroxyphenoxy)-1-phenyl-1H—pyrazolo[3,4-b]pyrazine | 47 |
| 78 | Cl—C$_6$H$_4$— | 5-(4-chlorophenoxy)-1-phenyl-1H—pyrazolo[3,4-b]pyrazine | 48 |
| 79 | Br—C$_6$H$_4$— | 5-(4-bromophenoxy)-1-phenyl-1H—pyrazolo[3,4-b]pyrazine | 49 |

(4) A = —OR$_6$

| Compound No. | R$_6$ | Name of Compound | Example No. |
|---|---|---|---|
| 80 | CH$_3$— | 5-methoxy-1-phenyl-1H—pyrazolo[3,4-b]pyrazine | 50 |
| 81 | C$_2$H$_5$— | 5-ethoxy-1-phenyl-1H—pyrazolo[3,4-b]pyrazine | 51 |
| 82 | C$_3$H$_7$— | 5-propoxy-1-phenyl-1H—pyrazolo[3,4-b]pyrazine | 52 |
| 83 | isoC$_3$H$_7$— | 5-isopropoxy-1-phenyl-1H—pyrazolo[3,4-b]pyrazine | 53 |
| 84 | C$_4$H$_9$— | 5-butoxy-1-phenyl-1H—pyrazolo[3,4-b]pyrazine | 54 |
| 85 | isoC$_4$H$_9$— | 5-isobutoxy-1-phenyl-1H—pyrazolo[3,4-b]pyrazine | 55 |
| 86 | secC$_4$H$_9$— | 5-sec-butoxy-1-phenyl-1H—pyrazolo[3,4-b]pyrazine | 56 |
| 87 | C$_5$H$_{11}$— | 5-pentyloxy-1-phenyl-1H—pyrazolo[3,4-b]pyrazine | 57 |
| 88 | isoC$_5$H$_{11}$— | 5-isopentyloxy-1-phenyl-1H—pyrazolo[3,4-b]pyrazine | 58 |
| 89 | C$_6$H$_{13}$— | 5-hexyloxy-1-phenyl-1H—pyrazolo[3,4-b]pyrazine | 59 |
| 90 | 2-C$_6$H$_{13}$— [(C$_4$H$_9$)(CH$_3$)CH—] | 5-(2-hexyloxy)-1-phenyl-1H—pyrazolo[3,4-b]pyrazine | 60 |
| 91 | C$_8$H$_{17}$— | 5-octyloxy-1-phenyl- | 61 |

-continued

(4) A = —OR₆

| Compound No. | R₆ | Name of Compound | Example No. |
|---|---|---|---|
| 92 | C₆H₅—CH₂— | 5-benzyloxy-1-phenyl-1H—pyrazolo[3,4-b]pyrazine | 62 |
| 93 | 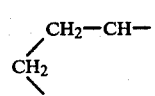 | 5-cyclohexyloxy-1-phenyl-1H—pyrazolo[3,4-b]pyrazine | 63 |
| 94 | C₃H₇—CH=CH—CH₂—(trans) | 5-(trans-2-hexenyloxy)-1-phenyl-1H—pyrazolo[3,4-b]pyrazine | 64 |
| 95 | (CH₃)₂N—CH₂=CH₂— | 5-(2-dimethylaminoethoxy)-1-phenyl-1H—pyrazolo[3,4-b]pyrazine | 65 |
| 96 | 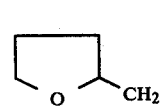 | 5-(2-tetrahydrofuryloxy)-1-phenyl-1H—pyrazolo[3,4-b]pyrazine | 66 |
| 97 | 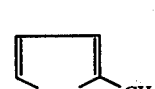 | 5-(2-furfuryloxy)-1-phenyl-1H—pyrazolo[3,4-b]pyrazine | 67 |

The compounds represented by the above formula (1) have excellent antitumor and/or antiviral activities and inhibit propagation of cancerous cells and virus. Accordingly, the compounds are useful as an antitumor or antiviral agent.

The preparation of the compounds of the present invention represented by the above formula (1) will now be described in detail with reference to the following Examples.

EXAMPLES 2 THROUGH 27

These Examples illustrate the preparation of compounds of the formula (1) in which A stands for a group

In a sealed tube, 23.1 g (0.1 mole) of 5-chloro-1-phenyl-1H-pyrazolo[3,4-b]pyrazine was reacted with 4 moles of an amine or nitrogen-containing heterocyclic compound shown in Table 1 at 220° C. for 3 hours, and the reaction product was dissolved in chloroform. The solution was washed with dilute hydrochloric acid and then with an aqueous 10% solution of sodium carbonate and dried with sodium sulfate. The solvent was removed by distillation and the residue was recrystallized from a recrystallization solvent shown in Table 1 to obtain a compound shown in Table 1. The melting points and IR analysis values of the so-obtained compounds are shown in Table 1.

TABLE 1

| Example No. | Intended Compound | Starting Amine | Crystal Form (Recrystallization Solvent) | Yield (%) | Melting Point (°C.) | IR ν$_{max}^{KBr}$ |
|---|---|---|---|---|---|---|
| 1 | 5-propylamino-1-phenyl-1H—pyrazolo[3,4-b]pyrazine | propylamine | yellow powder (hexane) | 78 | 94–95 | 3340 |
| 2 | 5-butylamino-1-phenyl-1H—pyrazolo[3,4-b]pyrazine | butylamine | yellow needle (methanol) | 75 | 90–92 | 3410 |
| 3 | 5-pentylamino-1-phenyl-1H—pyrazolo[3,4-b]pyrazine | pentylamine | light yellow needle (hexane) | 63 | 92–93 | 3330 |
| 4 | 5-hexylamino-1-phenyl-1H—pyrazolo[3,4-b]pyrazine | hexylamine | yellow column hexane | 59 | 88–89 | 3350, 2860, 2930 |
| 5 | 5-decanylamino-1-phenyl-1H—pyrazolo[3,4-b]pyrazine | decanylamine | yellow needle (methanol) | 57 | | 3350, 1590, 1500, 141 |
| 6 | 5-(2-hydroxyethylamino)-1-phenyl-1H—pyrazolo[3,4-b]pyrazine | 2-hydroxyethylamine | yellow powder (hexane) | 62 | 148–150 | 3300, 3350 |
| 7 | 5-(2-hydroxypropylamino)-1-phenyl-1H-13 pyrazolo[3,4-b]pyrazine | 2-hydroxypropylamine | orange powder (methanol) | 65 | 131–132 | 3340, 3470 |
| 8 | 5-(1-methylpropylamino)-1-phenyl-1H—pryazolo[3,4-b]pyrazine | 1-methylpropylamine | yellow prism (methanol) | 59 | | 3310, 1590, 1510, 141 |
| 9 | 5-(2-ethylhexylamino)-1-phenyl-1H—pyrazolo[3,4-b]pyrazine | 2-ethylhexylamine | yellow needle (methanol) | 67 | | 3340, 1590, 1510, 141 |
| 10 | 5-(3-carboxypropylamino)-1-phenyl-1H—pyrazolo[3,4-b]pyrazine | 3-carboxypropylamine | light yellow powder (methanol) | 76 | 151–153 | 1700 |
| 11 | 5-(5-carboxypentylamino)-1-phenyl-1H—pyrazolo[3,4-b]pyrazine | 5-carboxypentylamine | light yellow needle (methanol) | 69 | 151–153 | 1690 |
| 12 | 5-(2-chloroethylamino)-1-phenyl-1H—pyrazolo[3,4-b]pyrazine | 2-chloroethylamine | yellow needle (methanol) | 54 | | 3360, 1590, 1480, 141 |
| 13 | 5-(2-N,N—dimethylaminoethylamino)-1-phenyl-1H—pyrazolo[3,4-b]pyrazine | 2-N,N—dimethylaminoethylamine | yellow needle (hexane) | 63 | 121–122 | 3250 |
| 14 | 5-bezylamino-1-phenyl-1H—pyrazolo[3,4-b]pyrazine | benzylamine | orange needle (hexane) | 74 | 130–131 | 3340, 3050 |
| 15 | 5-(4-nitrobenzylamine)-1-phenyl-1H—pyrazolo[3,4-b]pyrazine | 4-nitrobenzylamine | yellow powder (methanol) | 68 | | 3300, 1520, 1410 |
| 16 | 5-(4-chlorobenzylamine)-1-phenyl-1H—pyrazolo[3,4-b]pyrazine | 4-chlorobenzylamine | yellow needle (methanol) | 63 | | 3310, 1600, 1410 |
| 17 | 5-(3-methylbenzylamine)-1-phenyl-1H—pyrazolo[3,4-b]pyrazine | 3-methylbenzylamine | yellow powder (methanol) | 71 | | 3330, 1600, 1410 |
| 18 | 5-dibutylamino-1-phenyl-1H-13 pyrazolo[3,4-b]pyrazine | dibutylamine | yellow needle (hexane) | 54 | 38–39 | 3010, 2990, 2920 |

TABLE 1-continued

| Example No. | Intended Compound | Starting Amine | Crystal Form (Recrystallization Solvent) | Yield (%) | Melting Point (°C.) | IR $\nu_{max}^{KBr}$ |
|---|---|---|---|---|---|---|
| 19 | 5-(2-hydroxyethylamino)-1-phenyl-1H-13 pyrazolo[3,4-b]pyrazine | 2-hydroxyethyl-methylamine | yellow plate (hexane) | 65 | 166–167 | 3400 |
| 20 | 5-benzylmethylamino-1phenyl-1H—pyrazolo[3,4-b]pyrazine | benzylmethylamine | yellow plate (hexane) | 59 | 131–132 | 3100 |
| 21 | 5-cyclopentylamino-1-phenyl-1H—pyrazolo[3,4-b]pyrazine | cyclopentylamine | yellow needle (methanol) | 78 | | 3350, 1600, 1490, 1410 |
| 22 | 5-cyclohexylamino-1-phenyl-1H—pyrazolo[3,4-b]pyrazine | cyclohexylamine | yellow powder (methanol) | 69 | | 3380, 1610, 1480, 1410 |
| 23 | 5-(4-methylcyclohexylamino)-1-phenyl-1H—pyrazolo[3,4-b]pyrazine | 4-methylcyclohexyl-amine | yellow scale (methanol) | 71 | | 3400, 1590, 1500, 1410 |
| 24 | 5-hydrazine-1-phenyl-1H—pyrazolo[3,4-b]pyrazine | hydrazine | yellow needle (methanol) | 80 | 193—195 | 3290 |
| 25 | 5-piperidino-1-phenyl-1H—pyrazolo-[3,4-b]pyrazine | piperidine | yellow scale (methanol) | 82 | 132–134 | 2930, 2850 |
| 26 | 5-(3-carboxypiperidino)-1-phenyl-1H—pyrazolo[3,4-b]pyrazine | nipecotic acid | yellow needle (methanol) | 68 | 192–194 | 1700 |
| 27 | 5-morpholino-1-phenyl-1H—pyrazolo-[3,4-b]pyrazine | morpholine | yellow scale (methanol) | 93 | 163–164 | 2950, 2850 |

EXAMPLES 28 THROUGH 38

In a sealed tube, 1.36 g (6 millimoles) of 5-chloro-1-phenyl-1H-pyrazolo[3,4-b]pyrazine was reacted with 25 millimoles of a phenylamine shown in Table 2 at 220° C. for 3 hours, and the reaction product was dissolved in chloroform. The solution was washed with 20 ml of 2N hydrochloric acid, then with 10 ml of an aqueous 2N solution of sodium carbonate and finally with 10 ml of water two times, and the washed solution was dried with anhydrous sodium sulfate. The solvent was removed by distillation under reduced pressure and the residue was recrystallized from a recrystallization solvent shown in Table 2 to obtain a compound shown in Table 2. The forms, yields, melting points and IR analysis values of the so-obtained compounds are shown in Table 2.

TABLE 2

| Example No. | R₃ | R₄ | Intended Compound | Phenylamine | Crystal Form (Recrystallization Solvent) | Yield (%) | Melting Point (°C.) | IR$\nu_{max}^{KBr}$cm$^{-1}$ (—NH) |
|---|---|---|---|---|---|---|---|---|
| 28 | phenyl | —H | 5-anilino-1-phenyl-1H—pyrazolo[3,4-b]pyrazine | aniline | yellow needle (benzene) | 94 | 188–189 | 3300 |
| 29 | phenyl | —CH₃ | 5-N—Methylanilino-1-phenyl-1H—pyrazolo[3,4-b]pyrazine | N-methylaniline | yellow needle (n-hexane) | 75 | 97–98 | 3280 |
| 30 | 3-methylphenyl | —H | 5-(2-toluidino)-1-phenyl-1H—pyrazolo[3,4-b]pyrazine | 2-toluidine | yellow needle (methanol) | 70 | 174–175 | 3300 |
| 31 | 3-methylphenyl | —H | 5-(3-toluidino)-1-phenyl-1H—pyrazolo[3,4-b]pyrazine | 3-toluidine | yellow needle (benzene) | 80 | 195–196 | 3270 |
| 32 | 2,3-dimethylphenyl | —H | 5-(2,3-dimethylanilino)-1-phenyl-1H—pyrazolo[3,4-b]pyrazine | 2,3-dimethylaniline | yellow needle (methanol) | 69 | 163–164 | 3290 |
| 33 | 4-butylphenyl | —H | 5-(4-butylanilino)-1-phenyl-1H—pyrazolo[3,4-b]pyrazine | 4-butylaniline | yellow scale (benzene-n-hexane) | 74 | 150–151 | 3320 |
| 34 | 2-methoxyphenyl | —H | 5-(2-anisidino)-1-phenyl-1H—pyrazolo[3,4-b]pyrazine | 2-anisidine | yellow needle (methanol) | 68 | 181–182 | 3340 |
| 35 | 4-ethoxyphenyl | —H | 5-(4-phenetidino)-1-phenyl-1H—pyrazolo[3,4-b]pyrazine | 4-phenetidine | yellow scale (methanol) | 70 | 206–207 | |

TABLE 2-continued

| Example No. | R₃ | R₄ | Intended Compound | Phenylamine | Crystal Form (Recrystallization Solvent) | Yield (%) | Melting Point (°C.) | IR $\nu_{max}^{KBr}$ cm⁻¹ (—NH) |
|---|---|---|---|---|---|---|---|---|
| 36 | 4-Cl-C₆H₄— | —H | 5-(4-chloroanilino)-1-phenyl-1H—pyrazolo[3,4-b]pyrazine | 4-Cl-C₆H₄—NH₂ | yellow powder (methanol) | 72 | 226–227 | 3300 |
| 37 | 4-F-C₆H₄— | —H | 5-(4-floroanilino)-1-phenyl-1H—pyrazolo[3,4-b]pyrazine | 4-F-C₆H₄—NH₂ | yellow needle (benzene) | 74 | 201–203 | 3300 |
| 38 | 3-O₂N-C₆H₄— | —H | 5-(3-nitroanilino)-1-phenyl-1H—pyrazolo[3,4-b]pyrazine | 3-O₂N-C₆H₄—NH₂ | yellow powder (methanol) | 60 | 261–263 | 3400 |

EXAMPLE 39

In 5.0 (0.053 mole) of phenol was dissolved 0.34 g (0.0085 mole) of sodium hydroxide, and 1.00 g (0.0043 mole) of 5-chloro-1-phenyl-1H-pyrazolo[3,4-b]pyrazine was added to the solution. The mixture was maintained at 150° C. for 2 hours. The reaction mixture was dissolved in chloroform, and the resulting solution was washed with an aqueous 10% solution of sodium hydroxide and then dried. The solvent was removed by distillation, and the residue was recrystallized from a benzene-hexane mixed solvent to obtain 1.20 g (the yield was 92%) of 5-phenoxy-1-phenyl-1H-pyrazolo[3,4-b]pyrazine in the form of a colorless needle crystal.

EXAMPLE 40

In 3 ml of dimethyl sulfoxide were dissolved 2.00 g (0.0115 mole) of p-bromophenol and 0.5 g (0.009 mole) of potassium hydroxide, and 1.00 g (0.0043 mole) of 5-chloro-1-phenyl-1H-pyrazolo[3,4-b]pyrazine was added to the solution. The mixture was maintained at 100° C. for 2 hours. The post treatments were conducted in the same manner as described in Example 39, and the resulting residue was recrystallized from hexane to obtain 1.41 g (the yield was 89%) of 5-(4-bromophenoxy)-1-phenyl-1H-pyrazolo[3,4-b]pyrazine in the form of a colorless scaly crystal.

EXAMPLES 41 THROUGH 49

The procedures of Example 40 were repeated by using phenol derivatives shown in Table 3, and the residues were recrystallized from recrystallization solvents shown in Table 3 to obtain intended compounds shown in Table 3.

The forms, melting points and IR analysis values of the intended compounds obtained in Examples 39 through 49 are shown in Table 3.

TABLE 3

| Example No. | $R_5$ | Phenol Derivative | Intented Compound | Form (Recrystallization Solvent) | Melting Point (°C.) | IR $\nu_{max}^{KBr}$ cm$^{-1}$ =C—O— | Others |
|---|---|---|---|---|---|---|---|
| 39 |  |  | 5-phenoxy-1-phenyl-1H—pyrazolo[3,4-b]pyrazine | c.n. (B + H) | 116~167 | 1335 1225 | |
| 40 |  | 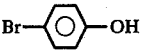 | 5-(4-buromo-phenoxy-1-phenyl-1H—pyrazolo[3,4-b]pyrazine | c.s. (H) | 171~172 | 1335 1250 | |
| 41 | 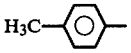 | 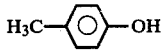 | 5-(4-methylphenoxy-1-phenyl-1H—pyrazolo[3,4-b]pyrazine | c.s. (B + H) | 144~145 | 1335 1255 | |
| 42 | 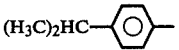 | 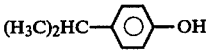 | 5-(4-isopropylphenoxy-1-phenyl-1H—pyrazolo[3,4-b]pyrazine | c.n. (H) | 114~115 | 1330 1250 | |
| 43 | 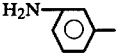 |  | 5-(3-aminophenoxy-1-phenyl-1H—pyrazolo[3,4-b]pyrazine | c.po. (M) | 173~174 | 1325 1245 | |
| 44 | 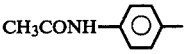 | 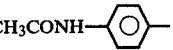 | 5-(4-acetamidophenoxy-1-phenyl-1H—pyrazolo[3,4-b]pyrazine | l.n. (C) | 253~254 | 1335 1250 | 1670 (CONH) |
| 45 | 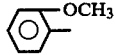 | 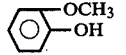 | 5-(2-methylphenoxy-1-phenyl-1H—pyrazolo[3,4-b]pyrazine | c.n. (M) | 145~146 | 1335 1250 | |
| 46 | 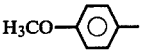 | 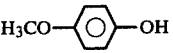 | 5-(4-methylphenoxy-1-phenyl-1H—pyrazolo[3,4-b]pyrazine | c.s. (B) | 163~164 | 1335 1245 | |
| 47 | 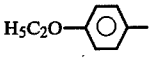 | 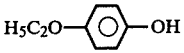 | 5-(4-ethoxyphenoxy-1-phenyl-1H—pyrazolo[3,4-b]pyrazine | c.n. (B + H) | 160~161 | 1335 1245 | |
| 48 | 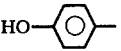 | 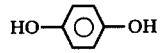 | 5-(4-hydroxyphenoxy-1-phenyl-1H—pyrazolo[3,4-b]pyrazine | c.pr. (B) | 206~207 | 1335 1245 | 3400 (OH) |

TABLE 3-continued

| Example No. | R5 | Phenol Derivative | Intented Compound | Form (Recrystallization Solvent) | Melting Point (°C.) | IR$\nu_{max}^{KBr}$cm$^{-1}$ =C—O— | Others |
|---|---|---|---|---|---|---|---|
| 49 | 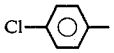 |  | 5-(4-chlorophenoxy-1-phenyl-1H—pyrazolo[3,4-b]pyrazine | c.s. (H) | 160~161 | 1335 1250 | |

Note
c ... colorless
l ... light yellow
n ... needle
s ... scale
pr ... prism
po ... powder
B ... benzene
H ... hexane
M ... methanol
C ... chloroform

EXAMPLES 50 THROUGH 55

In 50 ml of methanol was dissolved 2.1 g (0.091 mole) of metallic sodium, and then, 9.5 g (0.043 mole) of 1-phenyl-1H-phrazolo[3,4-b]pyrazine-5-carbonitrile was added to the solution. The mixture was heated under reflux for 3 hours. After completion of the reaction, the excessive amount of methanol was removed by distillation under a reduced pressure. The residue was washed with water, dried and then recrystallized from methanol to obtain 8.2 g (the yield was 84%) of 5-methoxy-1-phenyl-1H-pyrazolo[3,4-b]pyrazine in the form of a colorless needle crystal.

The above-mentioned procedures were repeated by using various alcohols shown in Table 4 (Examples No. 51 through 55) to obtain 1-phenyl-1H-pyrazolo[3,4-b]pyrazine derivatives having in the 5-positions —OR$_6$ substituents shown in Table 4.

The crystal forms, yields, melting points and IR analysis values of the resultant compounds are shown in Table 4.

EXAMPLES 56, 57 AND 58

In 50 ml of sec.-butanol was dissolved 2.1 g (0.091 mole) of metallic sodium, and then, 10.0 g (0.043 mole) of 5-chloro-phenyl-1H-pyrazolo[3,4-b]pyrazine was added to the solution. The mixture was heated under reflux for 2 hours. After completion of the reaction, the excessive amount of sec.-butanol was removed by distillation under a reduced pressure. The residue was washed with water, dried and then recrystallized from hexane to obtain 6.2 g (the yield was 53%) of 5-sec.-butoxy-1-phenyl-1H-pyrazolo[3,4-b]pyrazine in the form of a colorless needle crystal.

The above-mentioned procedures were repeated by using pentyl and iso-pentyl alcohols instead of sec.-butanol to obtain 1-phenyl-1H-pyrazolo[3,4-b]pyrazine derivatives having 5-pentyloxy and 5-iso-pentyloxy groups.

The crystal forms, yields, melting points and IR analysis values of the resultant compounds are shown in Table 4.

EXAMPLES 59 THROUGH 68

In 50 ml of hexanol was dissolved 2.1 g (0.091 mole) of metallic sodium, and then, 14.6 g (0.043 mole) of 5-(4-tolylsulfonyl)-1-phenyl-1H-pyrazolo[3,4-b]pyrazine was added to the solution. The mixture was heated under reflux for 2 hours. After completion of the reaction, the exessive amount of hexanol was removed by distillation under a reduced pressure. The residue was washed with water, dried and then recrystallized from a benzene/methanol (1:2) mixed solvent to obtain 11.5 g (the yield was 90%) of 5-hexyloxy-1-phenyl-1H-pyrazolo[3,4-b]pyrazine in the form of a colorless needle crystal.

The above-mentioned procedures were repeated by using various alcohols shown in Table 4 (Examples 60 through 68) to obtain 1-phenyl-1H-pyrazolo[3,4-b]pyrazine derivatives having in the 5-positions —OR$_6$ substituents shown in Table 4.

The crystal forms, yields, melting points and IR analysis values of the resultant compounds are shown in Table 4.

TABLE 4

| Example No. | R$_6$ | Alcohol | —OR$_6$ | Crystal form (Recrystallization Solvent) | Yield | Melting point | IR$\nu$KBr max (cm$^{-1}$) =c-o- |
|---|---|---|---|---|---|---|---|
| 50 | CH$_3$— | CH$_3$OH | 5-methyl- | c.n. (MeOH) | 84 | 105–107 | 1255 |
| 51 | C$_2$H$_5$— | C$_2$H$_5$OH | 5-ethoxy- | y.n. (MeOH) | 82 | 139–140 | 1255 |
| 52 | C$_3$H$_7$— | C$_3$H$_7$OH | 5-propoxy- | c.n. (MeOH) | 89 | 98–99 | 1250 |
| 53 | iso C$_3$H$_7$— | iso C$_3$H$_7$OH | 5-isoproxy- | ly.cu. (Hexane) | 86 | 86–87 | 1255 |
| 54 | C$_4$H$_9$— | C$_4$H$_9$OH | 5-butoxy- | c.sc. (MeOH) | 90 | 96–98 | 1243 |
| 55 | iso C$_4$H$_9$— | iso C$_4$H$_9$OH | 5-isobutoxy- | c.p. (MeOH) | 88 | 110–111 | 1252 |
| 56 | sec C$_4$H$_9$— | sec C$_4$H$_9$OH | 5-sec-butoxy- | c.n. (Hexane) | 53 | 61–62 | 1255 |
| 57 | C$_5$H$_{11}$— | C$_5$H$_{11}$OH | 5-pentyloxy- | c.sc. | 85 | 98–99 | 1250 |

TABLE 4-continued

| Example No. | R$_6$ | Alcohol | —OR$_6$ | Crystal form (Recrystal- lization Solvent) | Yield | Melting point | IR$\nu$KBr max (cm$^{-1}$) =c-o- |
|---|---|---|---|---|---|---|---|
| 58 | iso C$_5$H$_{11}$— | iso C$_5$H$_{11}$OH | 5-isopentyloxy- | ly.n. (MeOH) | 83 | 84–85 | 1250 |
| 59 | C$_6$H$_{13}$ | C$_6$H$_{13}$OH | 5-hexyloxy- | c.sc. (MeOH + Benzene) (1:2) | 90 | 107–108 | 1250 |
| 60 | 2-C$_6$H$_{13}$ | 2-C$_6$H$_{13}$OH | 5-(2-hexyloxy)- | c.liquid | 60 | | 1249 |
| 61 | C$_8$H$_{17}$ | C$_8$H$_{17}$OH | 5-octyloxy- | c.sc. (MeOH) | 81 | 110–111 | 1249 |
| 62 | PhCH$_2$— | PhCH$_2$OH | 5-benzyloxy- | c.sc. (MeOH) | 90 | 92–93 | 1252 |
| 63 | cyclopentyl-CH$_2$— | cyclopentyl-OH | 5-cyclohexyloxy- | c.sc. (MeOH) | 71 | 96–97 | 1249 |
| 64 | C$_3$H$_7$—CH=CH—CH$_2$— | C$_3$H$_7$—CH=CH—CH$_2$OH | 5-(trans-2-hexenyloxy)- | c.n. (Hexane) | 93 | 55–56 | 1250 |
| 65 | (CH$_3$)$_2$N—CH$_2$—CH$_2$ | (CH$_3$)$_2$N—CH$_2$—CH$_2$OH | 5-(2-dimethyl-aminoethyloxy)- | c.n. (Hexane) | 94 | 86–87 | 1255 |
| 67 | tetrahydrofurfuryl-CH$_2$— | tetrahydrofurfuryl-CH$_2$OH | 5-(2-tetrahydro-furfuryloxy) | c.leaflet (Hexane) | 79 | 88–89 | 1243 |
| 68 | furfuryl-CH$_2$— | furfuryl-CH$_2$OH | 5-(2-furfuryloxy)- | c.n (MeOH) | 91 | 125–126 | 1251 |

Note
c . . . Colorless
n . . . needle
ly . . . light yellow
y . . . yellow
sc . . . scale
cu . . . cubic
p . . . plate

We claim:

1. 1-phenyl-1H-pyrazolo[3,4-b]pyrazine compounds represented by the formula (1):

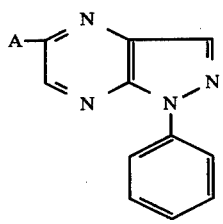

(1)

wherein A stands for:
(i) a group

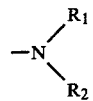

in which R$_1$ and R$_2$ stand for a hydrogen atom, an alkyl group having 1 to 10 carbon atoms, said alkyl group being unsubstituted or substituted by one or two substituents selected from the group consisting of a hydroxyl group, a carboxyl group, a halogen atom, a lower alkylamino group having 1 to 6 carbon atoms, a phenyl group which is unsubstituted or substituted by one or two substituents selected from the group consisting of an alkyl group having 1 to 6 carbon atoms, a halogen atom, a nitro group and a carboxyl group;
a cycloalkyl group having 5 to 8 carbon atoms, said cycloalkyl group being unsubstituted or substituted by one or two substituents selected from the group consisting of a hydroxyl group, an alkyl group having 1 to 6 carbon atoms, a halogen atom, a nitro group and a carboxyl group; and
an amino group; or
R$_1$ and R$_2$ form a nitrogen-containing saturated heterocyclic ring together with the nitrogen atom, to which R$_1$ and R$_2$ are bonded, said nitrogen-containing saturated heterocyclic ring being selected from the group consisting of pyrrolidinyl, imidazolidinyl, pyrazolidinyl, piperidinyl, piperazinyl and morpholinyl groups being unsubstituted or substituted by at least one substituent selected from the group consisting of a hydroxyl group, an alkyl group having 1 to 6 carbon atoms, a halogen atom, a nitro group and a carboxyl group;
(ii) a group

in which $R_3$ stands for a phenyl group, said phenyl group being unsubstituted or substituted by one or two substituents selected from the group consisting of a halogen atom, a lower alkyl group having 1 to 6 carbon atoms, a lower alkoxy group having 1 to 6 carbon atoms, a carboxyl group or a nitro group, and $R_4$ stands for a hydrogen atom, or a methyl or ethyl group;
(iii) a group —$OR_5$ in which $R_5$ stands for a phenyl group, said phenyl group being unsubstituted or substituted by one of two substituents selected from the group consisting of a halogen atom, a hydroxyl group, a lower alkyl group having 1 to 6 carbon atoms, a lower alkoxy group having 1 to 6 carbon atoms, an amino group or a lower alkylamide group having 1 to 6 carbon atoms; or
(iv) a group —$OR_6$ in which $R_6$ stands for an alkyl group having 1 to 10 carbon atoms said alkyl group being unsubstituted or substituted by one or two substituents selected from the group consisting of a halogen atom, an alkylamino group having 1 to 6 carbon atoms, a furanyl group, a tetrahydrofuranyl group, a phenyl group which is unsubstituted or substituted by one or two substituents selected from the group consisting of an alkyl group having 1 to 6 carbon atoms, a halogen atom, a nitro group and a carboxyl group; or
a cycloalkyl group having 5 to 8 carbon atoms.

2. 1-phenyl-1H-pyrazolo[3,4-b]pyrazine compounds according to claim 1 wherein the groups $R_1$ and $R_2$ in A of the formula (1) are independently selected from the group consisting of a hydrogen atom and linear and branched alkyl groups having 3 to 7 carbon atoms.

3. 1-phenyl-1H-pyrazolo[3,4-b]pyrazine compounds according to claim 1 wherein the group $R_3$ in A of the formula (1) is a phenyl group which is unsubstituted or substituted by a halogen atom or an alkyl group having 1 to 4 carbon atoms.

4. 1-phenyl-1H-pyrazolo[3,4-b]pyrazine compounds according to claim 1 wherein the group $R_5$ in A of the formula (1) is a phenyl group which is unsubstituted or substituted by a halogen atom or an alkyl group having 1 to 4 carbon atoms.

5. 1-phenyl-1H-pyrazolo[3,4-b]pyrazine compounds according to claim 1 wherein the group $R_6$ in A of the formula (1) is an alkyl group having 1 to 7 carbon atoms.

* * * * *